United States Patent [19]

Townsend et al.

[11] 4,092,305
[45] May 30, 1978

[54] ALKYL TRIAZENO URACIL COMPOUNDS AND METHOD OF PREPARATION THEREOF

[76] Inventors: Leroy B. Townsend, 3595 Apollo Dr., Salt Lake City, Utah 84117; T. Craig Thurber, 227 S. 13 East, Salt Lake City, Utah 84115

[21] Appl. No.: 623,909

[22] Filed: Oct. 20, 1975

Related U.S. Application Data

[63] Continuation of Ser. No. 282,362, Nov. 6, 1972, abandoned.

[51] Int. Cl.² ............................................. C07C 115/00
[52] U.S. Cl. ..................................... 260/140; 260/141; 424/226
[58] Field of Search ......................... 260/140; 424/226

[56] References Cited

U.S. PATENT DOCUMENTS

| | | | |
|---|---|---|---|
| 3,162,571 | 12/1964 | Adams et al. | 260/140 X |
| 3,206,357 | 9/1965 | Cannon et al. | 260/140 X |
| 3,649,613 | 3/1972 | Krauth et al. | 260/140 |
| 3,741,951 | 6/1973 | Hess et al. | 260/140 |
| 3,956,262 | 5/1976 | Heyes et al. | 260/140 |

OTHER PUBLICATIONS

Thurber et al., "A Structural Study of 5-Diazouracil, 5-Diazouridine and 5-Diazo-2-Deoxyuridine by PMR Spectroscopy and A Discussion of Certain Reactions in View of the Revised Structures." Aug. 23–27, 1971, Third International Congress of Heterocyclic Chemistry.

Shealy et al., "Imidazoles I Coupling Reactions of 5-Diazoimidazole-4-carboxamide", Journal of Organic Chemistry, vol. 27, 1962, 2150–2154.

Thurber et al., J. Hetero Chem. vol. 9, Jun., 1972, 629–636.

*Primary Examiner*—Charles F. Warren
*Attorney, Agent, or Firm*—Trask & Britt

[57] ABSTRACT

5-alkyl triazeno uracil compounds and derivatives thereof were synthesized by reacting an alkyl amine such as dimethylamine with a methonal adduct of 5-diazouracil and nucleosides thereof, under stringent reaction conditions to yield the desired compounds. These alkyl triazeno uracil compounds have the structure

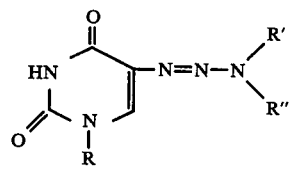

wherein R is hydrogen or a carbohydrate group, particularly a pentose or hexose monosaccharide such as ribose, arabinose, glucose, and the like, and R' and R" are lower alkyl groups having one to four carbon atoms and wherein R' and R" may be the same or different alkyl groups. The compounds of this invention have been found especially effective as antibacterial and antifungal agents and in inhibiting carcinoma growth in animal tissue.

16 Claims, No Drawings

ALKYL TRIAZENO URACIL COMPOUNDS AND METHOD OF PREPARATION THEREOF

This is a continuation, of application Ser. No. 282,362, filed Nov. 6, 1972, now abandoned.

BACKGROUND OF THE INVENTION

The structures of 5-diazouracil, 5-diazouridine and 5-diazo-2'-deoxyuridine have been the subject of several investigations. Originally, 5-diazouracil was prepared by decarboxylation of 5-diazoorotic acid(Behrend and Ernert, as reported in Ann. Chem., 258, 347 (1890). Several compounds were isolated in the Behrend and Ernert investigation, including an anhydride, a hydrate and an ethanol adduct of 5-diazouracil. These compounds were assigned, respectively, the following structures:

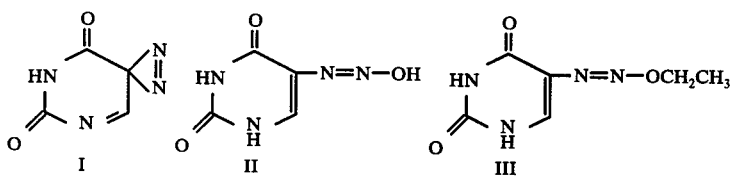

The assigned structures, however, have been reinvestigated. See Thurber and Townsend, *A Reinvestigation of the Structure for 5-diazouracil, 5-diazouridine, 5-diazo-2'-deoxyuridine and Certain Related Derivatives by Proton Magnetic Resonance Spectroscopy*, J. Hetero, Chem., 9, 629, (1972). This reinvestigation was conducted because the above-assigned structures failed to explain certain properties of 5-diazouracil and related compounds, and because 5-diazouracil and related compounds failed to react under conditions typical for diazo compounds.

SUMMARY OF INVENTION

The compounds of this invention are generically 5-alkyl triazenouracil, -uridine and -2'-deoxyuridine compounds having the structure

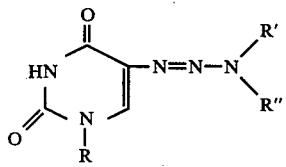

wherein R is hydrogen or a carbohydrate group, particularly a monosaccaride such as ribose, arabinose, glucose, and the like group and R' and R" are lower alkyl groups containing one to four carbon atoms, especially methyl and ethyl groups and wherein R' and R" may be the same or different groups.

Specific compounds include: 5-(3, 3-dimethyl-1-triazeno) uracil having the formula:

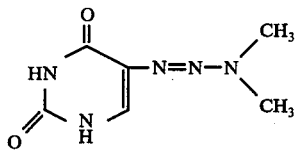

and uridine compounds such as 5-(3, 3-dimethyl-1-triazeno) uridine having the formula:

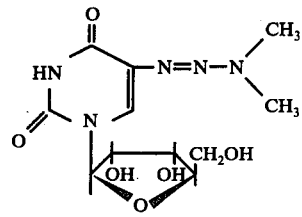

and 5-(3, 3-dimethyl-1-triazeno) -2'-deoxyuridine having the formula:

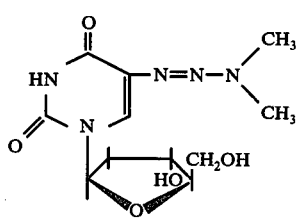

Although the above identified compounds are illustrative of compounds where R of structure IV is either hydrogen, ribose, or 2' deoxyribose, other carbohydrate groups, particularly monosaccaride groups are within the scope of the invention. Preferred carbohydrate compounds are those of eight carbons or less, particularly of six carbons or less wherein the R group is a monosaccaride. Monosaccarides which are stable adducts to the basic pyrimidine structure and which are sufficiently small to avoid sterically interfering with the desired reactions include ribose, including 2-deoxyribose, glucose, arabinose, pentose and hexose groups.

These compounds are of particular interest inasmuch as they have exhibited antibacterial, antifungal and anticancer activity.

The compounds of this invention are formed by reacting a pyrimidine compound, that is, a uracil or uridine, having the structure:

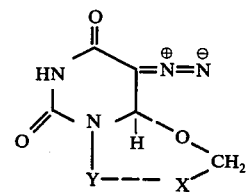

with a dialkylamine, including cyclic amines, for example, diethylamine, diproplyamine, dimethylamine, methyl ethylamine, methyl propylamine, ethylbutylamine, morpholine and the like. The reaction is preferably conducted at a temperature of above about 10° C. and preferably at temperatures at above at least about 20° C. The reaction may be conducted at atmospheric pressure, although super-atmospheric pressures are generally preferred to shorten the reaction time. Reaction under super-atmospheric conditions is generally conducted by placing the reactants in a sealed container, e.g. a laboratory bomb, capable of withstanding high pressures and placing same in an autoclave. The reaction pressure results from the increased temperature of the materials and the expulsion of gaseous reactants and reaction products. The reaction if conducted at ambient temperatures using a condensor if necessary to maintain a constant temperature condition.

The reaction proceeds well under fusion conditions, although solvents may be utilized if desired. Preferable solvents include ethylacetate, methylacetate and similar mildly polar solvents. Other solvents include higher alkyl acetates and alkyl ethers such as methyl ethyl ether, diethyl ether and the like. Mildly polar solvents such as ethylacetate and methylacetate are preferred inasmuch as aromatic solvents do not provide sufficient solubility of reactants to be useful while more polar solvents such as water, methanol, ethanol, acrylonitrile and the like cause ionization, resulting in a reaction which does not produce the desired compounds. Reaction under fusion conditions is generally preferred since the necessity of a separate solvent is eliminated.

The reaction temperature range is from about 10° C. to about 80° C. and preferably from about 20° to about 60° C. At temperature conditions higher than about 80° C., especially if a fusion reaction is being conducted, too much of the uridine or uracil reactant becomes soluble in the dimethylamine which can result in ionization yielding a product other than the desired product.

These reaction conditions are considered stringent for diazo compounds inasmuch as reactions involving diazo compounds are usually conducted about or below 0° C. At temperatures higher than about 0° C. diazo compounds are typically very unstable. It has been concluded that the stringent conditions are required to break the C—O—C bond at the six position (Structure VIII) without causing ionization to occur at the nitrogen atom in the three position (Structure VIII).

The triazeno compounds produced according to this invention have been found to be stable up to their respective melting points unless some of the alkylamine reactant is occluded. Occluded alkylamine, such as dimethylamine, tends to cause ionization and degradation of the reaction product.

The preparation of selected compounds of this invention is illustrated by the following examples:

EXAMPLE I

Preparation of 5-(3, 3-Dimethyl-1-triazeno) uracil

To 2.5 grams of 5-Diazouracil-methanol adduct (XI) was added 84 milliliters of ethylacetate at room temperature in a pressure bottle. This suspension was cooled to 0° C. and 10 milliliters of anhydrous dimethylamine were then added. The pressure bottle was sealed and heated in an oil bath of 40°–43° C. for 4 hours and then allowed to stand at 5° C. for 18 hours. The white solid was collected by filtration, washed with 10 milliliters of ethylacetate at room temperature, dissolved in 125 milliliters of methanol at room temperature and then stirred with Norit (100 milligrams) for 15 minutes. The Norit was removed by filtration and the filtrate concentrated (not to dryness) keeping the temperature below 20° C. to give a thick suspension. The precipitate was collected by filtration, washed with ethylacetate (15 milliliters) and then allowed to dry at room temperature to give 1.9 grams of product having a melting point of 162°–164° C., decomposing with explosion. An additional 0.56 grams of product was obtained from the methanol filtrate by evaporation to dryness in vacuo, to give a total product recovery of 2.46 grams (90% yield). A small sample was dissolved in methanol, treated with Norit, the Norit removed by filtration and the filtrate evaporated to dryness. This solid was dired at 100° C. under 0.2 Tr vacuum over $P_4O_{10}$ to afford an analytical sample, melting point 166°–167° C.;

uv: $\lambda_{max}^{MeOH}$, 263 nm ($\epsilon$ 16, 500).

Anal. Calcd. for $C_6H_9N_5O_2$: C, 39.34; H, 4.95; N, 38.23. Found: C, 39.39; H, 4.98; N, 38.39.

EXAMPLE II

Preparation of 5-(3, 3-Dimethyl-1-triazeno) uridine (VI).

To 10.0 grams of $O^{5'}$-6(S)-cyclo-5-diazouridine was added 200 milliliters of ethylacetate and this reaction mixture divided equally into two separate pressure bottles. These reaction mixtures were then cooled to 0° C. in an ice-salt bath and 25 milliliters of anhydrous dimethylamine added to each vessel. The pressure bottles were sealed, covered with aluminum foil and allowed to stand at room temperature for 1 hour with occasional shaking. They were then heated in an oil bath at 52°–55° C. with vigorous stirring for 4 hours. The source of heat was removed, the oil bath allowed to slowly cool and the reaction mixture stirred for an additional 16 hours.

The pressure bottles were cooled to 0° C and the solutions combined. The oil which remained in the reaction vessels was dissolved in a minimum amount of methanol (approximately 50 milliliters) and this was added to the ethylacetate solution. This solution was evaporated in vacuo in an oil while maintaining the temperature below 30° C. The oil was triturated with ethylacetate (50 milliliters) and scratching with an aluminum spatula produced a light yellow solid which was collected by filtration and washed with ethylacetate (25 milliliters). An additional quantity of product was obtained from the filtrate by repeating the above procedure (evaporation and trituration) to give a total yield of 10.6 grams, which softened at 122°–126° C. and melted at 130°–138° C.

This solid was recrystallized from boiling acetonitrile (500 milliliters) with sufficient methanol added to effect a clear solution. Two crops were obtained by isolation, volume reduction to 250 milliliters in vacuo and the addition of 20 milliliters of ethylacetate to give 9.2 grams of product (79% yield) having a melting point of 136°–138° C. An analytical sample was obtained by recrystallization from acetonitrile and dried in an Abderhalden apparatus over isopropanol at reflux temperature of 1.5 hours over $P_4O_{10}$, melting point 170°–172° C; uv: $\lambda_{max}^{MeOH}$, 322 nm ($\epsilon$ 11,800), 271 nm ($\epsilon$ 10,700).

Anal. Calcd. for $C_{11}N_{17}N_5O_6$: C, 41.91; H, 5.43; N, 22.21. Found: C, 41.96; H, 5.49; N, 22.12.

EXAMPLE III

Preparation of 5-(3, 3-Dimethyl-1-triazeno)-2'-deoxyurdine (VII).

Anhydrous dimethylamine (10 milliliters) was added to 150 milligrams of $O^{5'}$-6(S)-cyclo-5-diazo-2'-deoxyuridine and the solution stirred and allowed to reflux (dry ice-acetone condensor) at room temperature for 1.5 hours. The solution was evaporated to dryness in vacuo (38°) to give a fine white crystalline material. Ethylacechromatography on silica gel to afford N-t-butoxycarbonyl-L-tyrosylglycylglycine benzyl ester.

EXAMPLE 4

To a solution of 2.8 parts N-t-butoxycarbonyl-L-tyrosylglycylclycine benzyl ester in 160 parts methanol is added 0.4 part palladium black metal catalyst. The resulting mixture is shaken with hydrogen at room temperature at atmospheric pressure for about 5 hours. The catalyst is then removed by filtration, and the solvent removed by evaporation at reduced pressure. The resulting crude material is purified using low pressure chromatography to afford N-t-butoxycarbonyl-L-tyrosylglycylglycine.

EXAMPLE 5

A solution of 26.6 parts N-t-butoxycarbonyl-L-tryptophan 2,4,5-trichlorophenyl ester and 12.0 parts L-methionine benzyl ester in 200 parts methylene chloride is stirred overnight at room temperature. The solvent is then removed by evaporation under reduced pressure. The crude dipeptide is then subjected to low-pressure column chromatography on silica gel to afford N-t-butoxycarbonyl-L-tryptophyl-L-methionine benzyl ester.

EXAMPLE 6

17.1 Parts N-t-butoxycarbonyl-L-tryptophyl-L-methionine benzyl ester is dissolved in 200 parts dioxane and treated with a 10 fold excess of 2N hydrochloric acid in dioxane for 10 minutes. Removal of the solvent under reduced pressure affords pure L-tryptophyl-L-methionine benzyl ester hydrochloride.

EXAMPLE 7

10.0 Parts N-t-butoxycarbonyl-L-tyrosylglycylglycine and 2.4 parts N-methylmorpholine are dissolved in 125 parts dimethylformamide and cooled to −15° C. Then 3.8 parts isobutyl chloroformate is added dropwise over a 30 minute period while maintaining the temperature at −15° C. Then, a solution of 12.7 parts L-tryptophyl-L-methionine benzyl ester hydrochloride in 50 parts dimethylformamide is slowly added at −15° C. and the mixture is stirred at this temperature for 30 minutes. The cooling apparatus is removed and the mixture is stirred at ambient temperature for an additional 2 hours. The product is isolated by diluting the reaction mixture with 10 volumes water and extracting with ethyl acetate. The ethyl acetate extracts are combined, dried over anhydrous sodium sulfate and stripped to dryness under reduced pressure. Purification of the residue by low pressure column chromatography affords N-t-butoxycarbonyl-L-tyrosylglycylglycyl-L-tryptophyl-L-methionine benzyl ester.

EXAMPLE 8

21.1 Parts N-t-butoxycarbonyl-L-tyrosylglycylglycyl-L-tryptophyl-L-methionine benzyl ester is dissolved in 70 parts methanol and the solution cooled to 10° C. Then, 90 parts by volume of 1 N sodium hydroxide solution is added dropwise with stirring while maintaining the temperature below 20° C. After standing at room temperature for 1 hour, the methanol is removed by evaporation under reduced pressure. The solution is washed once with ethyl ether to remove benzyl alcohol and the aqueous layer acidified with 90 parts by volume 1 N hydrochloric acid. The solid which results is filtered and washed with water to afford N-t-butoxycarbonyl-L-tyrosylglycylglycyl-L-tryptophyl-L-methionine.

The N-t-butoxycarbonyl-L-tyrosylglycylglycyl-L-tryptophyl-L-methionine is dissolved in 100 parts dioxane and stirred with a ten-fold excess of 2 N hydrochloric acid at room temperature for 15 minutes. The solvent is then removed under reduced pressure and the residue is triturated with ethyl ether. The resulting solid is precipitated from the mixture of methanol and ether to afford L-tyrosylglycylglycyl-L-tryptophyl-L-methionine hydrochloride. This compound is represented by the following formula

H-Tyr-Gly-Gly-Trp-Met-OH . HCl

EXAMPLE 9

The hydrochloride acid addition salt may be converted into other suitable salts, or to the free base, by standard procedures, such as ion exchange methods.

17.3 Parts L-tyrosylglycylglycyl-L-tryptophyl-L-methionine hydrochloride is dissolved in 250 parts by volume of 20% acetic acid and passed slowly through an IR-45 ion exchange column in the acetate form. The column is washed with 20% acetic acid until no more peptide is eluted. Fractions containing the product are combined and the solvent removed by stripping under reduced pressure at room temperature. The residual glass is dissolved in 75 parts water and lyophilized to give L-tyrosylglycylglycyl-L-tryptophyl-L-methionine acetic acid salt. This compound is represented by the following formula H-Tyr-Gly-Gly-Trp-Met-OH . acetic acid When water is substituted for the 20% acetic acid above, and a hydroxide ion exchange column is used, the above procedure gives the free base, which is represented by the following formula

H-Tyr-Gly-Gly-Trp-Met-OH

EXAMPLE 10

When an equivalent quantity of N-t-butoxycarbonyl-L-tyrosine 2,4,5-trichlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonyl-L-tyrosyl-L-methionine benzyl ester.

Treatment of the above dipeptide with 2 N hydrochloric acid as set out in Example 6 affords L-tyrosyl-L-methionine benzyl ester hydrochloride.

EXAMPLE 11

When an equivalent quantity of L-tyrosyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl-L-tyrosyl-L-methionine benzyl ester. Repetition of the procedure detailed in Example 8 using an equivalent quantity of N-t-butoxycarbonyl-L-tyrosyl-glycylglycyl-L-tyrosyl-L-methionine benzyl ester affords L-tyrosylglycylglycyl-L-tyrosyl-L-methionine hydrochloride. This compound is represented by the following formula

H-Tyr-Gly-Gly-Tyr-Met-OH.HCl

EXAMPLE 12

When an equivalent quantity of N-t-butoxycarbonyl-p-t-butyl-L-phenylalanine pentachlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonyl-p-t-butyl-L-phenylalanyl-L-methionine benzyl ester.

Treatment of the above dipeptide with 2 N hydrochloric acid as set out in Example 6 affords p-t-butyl-L-phenylalanyl-L-methionine benzyl ester hydrochloride.

EXAMPLE 13

When an equivalent quantity of p-t-butyl-L-phenylalanyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl-p-t-butyl-phenylalanyl-L-methionine benzyl ester.

Repetition of the procedure detailed in Example 8 using an equivalent quantity of N-t-butoxycarbonyl-L-tyrosylglycylglycyl-p-t-butyl-L-phenylalanyl-L-methionine benzyl ester affords L-tyrosylglycylglycyl-p-t-butyl-L-phenylalanyl-L-methionine hydrochloride. This compound is represented by the following formula

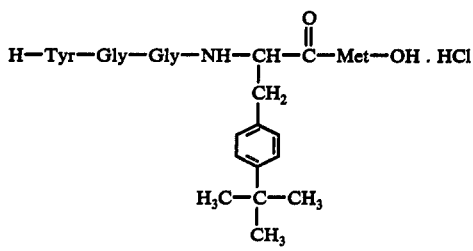

EXAMPLE 14

When an equivalent quantity of N-t-butoxycarbonyl-hexahydro-L-phenylalanine pentachlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonylhexahydro-L-phenylalanyl-L-methionine benzyl ester.

Treatment of the above dipeptide with 2 N hydrochloric acid as set out in Example 6 affords hexahydro-L-phenylalanyl-L-methionine benzyl ester hydrochloride.

EXAMPLE 15

When an equivalent quantity of hexahydro-L-phenylalanyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycylhexahydro-L-phenylalanyl-L-methionine benzyl ester.

Repetition of the procedure detailed in Example 8 using an equivalent quantity of N-t-butoxycarbonyl-L-tyrosylglycylglycylhexahydro-L-phenylalanyl-L-methionine benzyl ester affords L-tyrosylglycylglycylhexahydro-L-phenylalanyl-L-methionine hydrochloride. This compound is represented by the following formula

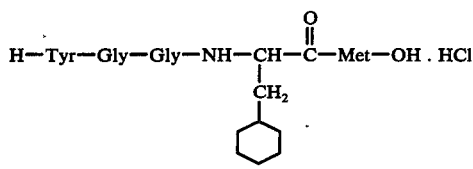

EXAMPLE 16

When an equivalent quantity of N-t-butoxycarbonyl-β-(2-thienyl)-L-alanine 2,4,5-trichlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonyl-β-(2-thienyl)-L-alanyl-L-methionine benzyl ester.

Treatment of the above dipeptide with 2 N hydrochloric acid as set out in Example 6 affords β-(2-thienyl)-L-alanyl-L-methionine benzyl ester hydrochloride.

EXAMPLE 17

When an equivalent quantity of β-(2-thienyl)-L-alanyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl β-(2-thienyl)-L-alanyl-L-methionine benzyl ester.

Repetition of the procedure detailed in Example 8 using an equivalent quantity of N-t-butoxycarbonyl-L-tyrosylclycylglycyl-β-(2-thienyl)-L-alanyl-L-methionine benzyl ester affords L-tyrosylglycylglycyl-β-(2-thienyl)-L-alanyl-L-methionine hydrochloride. This compound is represented by the following formula

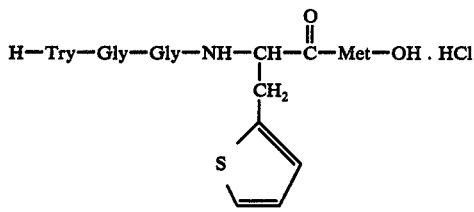

EXAMPLE 18

A solution of 19.5 parts N-t-butoxycarbonylglycine 2,4,5-trichlorophenyl ester and 11.1 parts L-leucine benzyl ester in 200 parts methylene chloride is stirred overnight at room temperature. The solvent is then removed by evaporation under reduced pressure. The crude dipeptide is then subjected to low-pressure column chromatography on silica gel to afford N-t-butoxycarbonylglycyl-L-leucine benzyl ester.

Treatment of the above dipeptide with 2 N hydrochloric acid as set out in Example 6 affords glycyl-L-leucine benzyl ester hydrochloride.

EXAMPLE 19

When an equivalent quantity of glycyl-L-leucine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycylglycyl-L-leucine benzyl ester.

Repetition of the procedure detailed in Example 8 using an equivalent quantity of N-t-butoxycarbonyl-L-tyrosylglycylglycylglycyl-L-leucine benzyl ester affords L-tyrosylglycylglycylglycyl-L-leucine hydrochloride. This compound is represented by the following formula H-Tyr-Gly-Gly-Gly-Leu-OH.HCl

EXAMPLE 20

When an equivalent quantity of N-t-butoxycarbonylD-tyrosine 2,4,5-trichlorophenyl ester is substituted for the N-t-butoxycarbonyl-L-tryptophan 2,4,5-trichlorophenyl ester of Example 5 and the procedure detailed therein substantially repeated, there is obtained N-t-butoxycarbonylD-tyrosyl-L-methionine benzyl ester.

Treatment of the above dipeptide with 2 N hydrochloric acid as set out in Example 6 affords D-tyrosyl-L-methionine benzyl ester hydrochloride.

EXAMPLE 21

When an equivalent quantity of D-tyrosyl-L-methionine benzyl ester hydrochloride is substituted for the L-tryptophyl-L-methionine benzyl ester hydrochloride of Example 7 and the procedure detailed therein substantially repeated, there is obtained N-t-butoxycarbonyl-L-tyrosylglycylglycyl-D-tyrosyl-L-methionine benzyl ester.

Repetition of the procedure detailed in Example 8 using an equivalent quantity of N-t-butoxycarbonyl-L-tyrosylglycylglycyl-D-tyrosyl-L-methionine benzyl ester affords L-tyrosylglycylglycyl-D-tyrosyl-L-methionine hydrochloride. This compound is represented by the following formula H-Tyr-Gly-Gly-Tyr-Met-OH.HCl(L,D,L)

What we claim is:
1. A compound of the formula

H-Tyr-Gly-Gly-W-Y-OH wherein Y is Leu or Met; W is β-thienyl-Ala; and the stereochemical configuration of each of the optically active amino acid residues may independently be D, L, or DL.

2. The compound according to claim 1 which is L-tyrosylglycylglycyl-β-thienyl-L-alanyl-L-leucine.

3. The compound according to claim 1 which is L-tyrosylglycylglycyl-β-thienyl-L-alanyl-L-methionine.

* * * * *